United States Patent
Hinderer et al.

(10) Patent No.: US 11,117,942 B2
(45) Date of Patent: Sep. 14, 2021

(54) AAV-EPO FOR TREATING COMPANION ANIMALS

(71) Applicant: The Trustees of the University of Pennsylvania, Philadelphia, PA (US)

(72) Inventors: Christian Hinderer, Philadelphia, PA (US); James M. Wilson, Philadelphia, PA (US); Matthew Wilson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 583 days.

(21) Appl. No.: 15/754,931

(22) PCT Filed: Aug. 30, 2016

(86) PCT No.: PCT/US2016/049487
§ 371 (c)(1),
(2) Date: Feb. 23, 2018

(87) PCT Pub. No.: WO2017/040524
PCT Pub. Date: Mar. 9, 2017

(65) Prior Publication Data
US 2018/0251508 A1 Sep. 6, 2018

Related U.S. Application Data

(60) Provisional application No. 62/336,211, filed on May 13, 2016, provisional application No. 62/212,144, filed on Aug. 31, 2015.

(51) Int. Cl.
| | | |
|---|---|---|
| *C12N 15/864* | (2006.01) | |
| *C07K 14/505* | (2006.01) | |
| *A61K 48/00* | (2006.01) | |
| *A61K 9/00* | (2006.01) | |
| A61K 38/00 | (2006.01) | |
| A61P 13/12 | (2006.01) | |

(52) U.S. Cl.
CPC .......... *C07K 14/505* (2013.01); *A61K 9/0019* (2013.01); *C12N 15/864* (2013.01); *A61K 38/00* (2013.01); *A61P 13/12* (2018.01); *C07K 2319/02* (2013.01); *C12N 2750/14143* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 5,139,941 A | 8/1992 | Muzyczka et al. | |
| 5,478,745 A | 12/1995 | Samulski et al. | |
| 5,741,683 A | 4/1998 | Zhou et al. | |
| 6,057,152 A | 5/2000 | Samulski et al. | |
| 6,204,059 B1 | 3/2001 | Samulski et al. | |
| 6,268,213 B1 | 7/2001 | Samulski et al. | |
| 6,491,907 B1 | 12/2002 | Rabinowitz et al. | |
| 6,596,535 B1 | 7/2003 | Carter | |
| 6,660,514 B1 | 12/2003 | Zolotukhin et al. | |
| 6,696,411 B1 * | 2/2004 | MacLeod | C07K 14/505 424/85.1 |
| 6,951,753 B2 | 10/2005 | Shenk et al. | |
| 7,094,604 B2 | 8/2006 | Snyder et al. | |
| 7,125,717 B2 | 10/2006 | Carter | |
| 7,172,893 B2 | 2/2007 | Rabinowitz et al. | |
| 7,201,898 B2 | 4/2007 | Monahan et al. | |
| 7,229,823 B2 | 6/2007 | Samulski et al. | |
| 7,282,199 B2 | 10/2007 | Gao et al. | |
| 7,439,065 B2 | 10/2008 | Ferrari et al. | |
| 7,456,683 B2 | 11/2008 | Takano et al. | |
| 7,588,772 B2 | 9/2009 | Kay et al. | |
| 7,790,449 B2 | 9/2010 | Gao et al. | |
| 7,906,111 B2 | 3/2011 | Wilson et al. | |
| 2007/0036760 A1 | 2/2007 | Wilson et al. | |
| 2009/0197338 A1 | 8/2009 | Vandenberghe et al. | |
| 2010/0093608 A1 * | 4/2010 | Tian | A61K 47/60 514/1.1 |
| 2011/0008363 A1 * | 1/2011 | Meisel | A61P 9/10 424/158.1 |
| 2011/0177967 A1 | 7/2011 | Carstens et al. | |
| 2012/0058102 A1 | 3/2012 | Wilson | |
| 2015/0230430 A1 | 8/2015 | Wilson | |

FOREIGN PATENT DOCUMENTS

| | | |
|---|---|---|
| EP | 1520589 | 4/2005 |
| EP | 1310571 | 2/2006 |
| WO | WO 97/26336 | 7/1997 |
| WO | WO 200015772 * | 3/2000 |
| WO | WO-2003/042397 | 5/2003 |
| WO | WO-2005/033321 | 4/2005 |
| WO | WO-2006/110689 | 10/2006 |
| WO | WO 2006/120030 | 11/2006 |

(Continued)

OTHER PUBLICATIONS

Walker et al, Expression of erythropoietin in cats treated with a recombinant adeno-associated viral vector, AJVR, vol. 66, No. 3, Mar. 2005, pp. 450-456.*
Gupta, S, Codon Optimziation, May 2003, pp. 1-13.*
Beall, et al., Transfer of the feline erythropoietin gene to cats using a recombinant adeno-associated virus vector, Gene Ther., vol. 7(6):534-9:534-39, Nov. 2009.
Buning et al., Recent developments in adeno-associated virus vector technology, J. Gene Med., vol. 10:717-733, May 2008.
Fisher et al., Transduction with Recombinant Adeno-Associated Virus for Gene Therapy is Limited by Leading-Strand Synthesis, J. Virol., vol. 70(1):520-532, Jan. 1996.
Grieger & Samulski, Adeno-associated virus as a gene therapy vector: Vector development, production and clinical applications, Adv. Biochem. Engin/Biotechnol, vol. 99:119-145, Oct. 2005.

(Continued)

*Primary Examiner* — Maria Marvich
(74) *Attorney, Agent, or Firm* — Howson & Howson LLP

(57) ABSTRACT

Compositions and methods are provided for treating companion animals are provided. An adeno-associated viral vector is provided which includes a nucleic acid molecule comprising a sequence encoding erythropoietin (EPO). In desired embodiments, the subject is a cat or dog.

20 Claims, 3 Drawing Sheets
Specification includes a Sequence Listing.

(56) References Cited

FOREIGN PATENT DOCUMENTS

| WO | 2010/0036964 | | 4/2010 |
|---|---|---|---|
| WO | WO 2010/036964 | | 4/2010 |
| WO | WO 2010129021 | * | 11/2010 |
| WO | WO-2011/126808 | | 10/2011 |
| WO | WO-2013/049493 | | 4/2013 |
| WO | 2014/0182684 | | 11/2014 |
| WO | WO 2014/182684 | | 11/2014 |
| WO | WO-2015/012924 | | 1/2015 |
| WO | PCT/US2016/049487 | | 2/2017 |
| WO | WO 2010/129021 | | 11/2020 |

OTHER PUBLICATIONS

McCarty et al., Self-complementary recombinant adeno-associated virus (scAAV) vectors promote efficient transduction independently of DNA synthesis, Gene Therapy, vol. 8(16):1248-1254, Aug. 2001.

Miyatake, et al., Transcriptional targeting of herpes simplex virus for cell-specific replication, J. Virol., vol. 71(7):5124-32, Jul. 1997.

Sandig et al., HBV-derived promoters direct liver-specific expression of an adenovirally transduced LDL receptor gene, Gene Ther., vol. 3(11):1002-9, Nov. 1996.

Thomson, et al., Nucl. Acids. Res., A comprehensive comparison of multiple sequence alignments, vol. 27(13):2682-2690, Jul. 1999.

Zhang et al., Adenovirus-adeno-associated virus hybrid for large-scale recombinant adeno-associated virus production, Human Gene Therapy, vol. 20:922-929, Sep. 2009.

GenBank Submission U00685, Felis domesticus erythropoietin mRNA, Jan. 8, 2017.

Walker, M.C. et al., Expression of erythropoietin in cats treated with a recombinant adeno-associated viral vector, Am J Vet Res. Mar. 2005;66(3):450-6.

Zeltner et al., Near-perfect infectivity of wild-type AAV as benchmark for infectivity of recombinant AAV vectors, Gene Ther. Jul. 2010;17(7):872-9.

* cited by examiner

FIG. 3A

SEQ ID NO: 3 CANINE EPO

MCEPAPPKPTQSAWHSFPECPALLLLLSLLLLPLGLPVLGAPPRLICDSRVLERYILE
AREAENVTMGCAQGCSFSENITVPDTKVNFYTWKRMDVGQQALEVWQGLALLSE
AILRGQALLANASQPSETPQLHVDKAVSSLRSLTSLLRALGAQKEAMSLPEEASPA
PLRTFTVDTLCKLFRIYSNFLRGKLTLYTGEACRRGDR

FIG. 3B

SEQ ID NO: 4 FELINE EPO

MGSCECPALLLLLSLLLLPLGLPVLGAPPRLICDSRVLERYILEAREAENVTMGCAE
GCSFSENITVPDTKVNFYTWKRMDVGQQAVEVWQGLALLSEAILRGQALLANSSQ
PSETLQLHVDKAVSSLRSLTSLLRALGAQKEATSLPEATSAAPLRTFTVDTLCKLFRI
YSNFLRGKLTLYTGEACRRGDR

SEQUENCE LISTING

<160> NUMBER OF SEQ ID NOS: 9

<210> SEQ ID NO 1
<211> LENGTH: 5791
<212> TYPE: DNA
<213> ORGANISM: Artificial Sequence
<220> FEATURE:
<223> OTHER INFORMATION: constructed sequence
<220> FEATURE:
<221> NAME/KEY: misc_feature
<222> LOCATION: (12)..(629)
<223> OTHER INFORMATION: Epo
<220> FEATURE:
<221> NAME/KEY: polyA_signal
<222> LOCATION: (696)..(822)
<223> OTHER INFORMATION: Rabbit\globin\poly\A
<220> FEATURE:
<221> NAME/KEY: repeat_region
<222> LOCATION: (911)..(1040)
<223> OTHER INFORMATION: 3' ITR (complement)
<220> FEATURE:
<221> NAME/KEY: rep_origin
<222> LOCATION: (1217)..(1672)
<223> OTHER INFORMATION: f1/ori (complement)
<220> FEATURE:
<221> NAME/KEY: misc_feature
<222> LOCATION: (1803)..(2660)
<223> OTHER INFORMATION: AP(R)
<220> FEATURE:
<221> NAME/KEY: rep_origin
<222> LOCATION: (2834)..(3422)
<223> OTHER INFORMATION: origin of replication
<220> FEATURE:
<221> NAME/KEY: repeat_region
<222> LOCATION: (3862)..(3991)
<223> OTHER INFORMATION: 5' ITR
<220> FEATURE:
<221> NAME/KEY: repeat_region
<222> LOCATION: (4059)..(4440)
<223> OTHER INFORMATION: CMV\IE\promoter
<220> FEATURE:
<221> NAME/KEY: promoter
<222> LOCATION: (4443)..(4724)
<223> OTHER INFORMATION: CB promoter
<220> FEATURE:
<221> NAME/KEY: TATA_signal
<222> LOCATION: (4697)..(4700)
<220> FEATURE:
<221> NAME/KEY: Intron
<222> LOCATION: (4819)..(5791)
<223> OTHER INFORMATION: chicken\beta-actin\intron

<400> SEQUENCE: 1

```
aattcgccac catgtgcgag cctgcccccc ctaagcctac acagtctgcc tggcacagct      60
tccccgagtg tcctgctctc ctgctgctgc tgagtttgct gctgctgcct ctgggcctgc     120
ctgtgctggg agcacctcct agactgatct gcgacagccg ggtgctggaa cggtacatcc     180
tggaagcccg cgaggccgag aatgtgacca tgggatgtgc ccagggctgc agcttcagcg     240
agaacatcac cgtgcccgac accaaagtga acttctacac ctggaagaga atggacgtgg     300
gccagcaggc cctggaagtg tggcagggac tggccctgct gtctgaggcc atcctgagag     360
gacaggctct gctggccaat gccagccagc ctagcgagac acctcagctg cacgtggaca     420
aggccgtgtc ctccctgaga agcctgacca gcctgctgag agcactggga gcccagaaag     480
aagccatgag cctgcctgag gaagccagcc ctgcccctct gagaaccttc accgtggaca     540
ccctgtgcaa gctgttccgg atctacagca acttcctgcg gggcaagctg accctgtaca     600
ccggcgaggc ttgtcggaga ggcgacagat gatgaggtac ctctagagtc gacccggggcg     660 gcctcgagga cggggtgaac tacgcctgag gatccgatct ttttccctct gccaaaaatt     720
```

-continued

```
atggggacat catgaagccc cttgagcatc tgacttctgg ctaataaagg aaatttattt      780
tcattgcaat agtgtgttgg aattttttgt gtctctcact cggaagcaat tcgttgatct      840
gaatttcgac cacccataat acccattacc ctggtagata agtagcatgg cgggttaatc      900
attaactaca aggaacccct agtgatggag ttggccactc cctctctgcg cgctcgctcg      960
ctcactgagg ccgggcgacc aaaggtcgcc cgacgcccgg gctttgcccg ggcggcctca     1020
gtgagcgagc gagcgcgcag ccttaattaa cctaattcac tggccgtcgt tttacaacgt     1080
cgtgactggg aaaaccctgg cgttacccaa cttaatcgcc ttgcagcaca tccccctttc     1140
gccagctggc gtaatagcga agaggcccgc accgatcgcc cttcccaaca gttgcgcagc     1200
ctgaatggcg aatgggacgc gccctgtagc ggcgcattaa gcgcggcggg tgtggtggtt     1260
acgcgcagcg tgaccgctac acttgccagc gccctagcgc ccgctccttt cgctttcttc     1320
ccttcctttc tcgccacgtt cgccggcttt ccccgtcaag ctctaaatcg gggctccct     1380
ttagggttcc gatttagtgc tttacggcac ctcgacccca aaaaacttga ttagggtgat     1440
ggttcacgta gtgggccatc gccctgatag acggttttc gccctttgac gttggagtcc     1500
acgttcttta atagtggact cttgttccaa actggaacaa cactcaaccc tatctcggtc     1560
tattcttttg atttataagg gattttgccg atttcggcct attggttaaa aaatgagctg     1620
atttaacaaa aatttaacgc gaattttaac aaaatattaa cgcttacaat ttaggtggca     1680
cttttcgggg aaatgtgcgc ggaacccta tttgtttatt tttctaaata cattcaaata     1740
tgtatccgct catgagacaa taaccctgat aaatgcttca ataatattga aaaggaaga     1800
gtatgagtat tcaacatttc cgtgtcgccc ttattccctt ttttgcggca ttttgccttc     1860
ctgttttgc tcacccagaa acgctggtga agtaaaaga tgctgaagat cagttgggtg     1920
cacgagtggg ttacatcgaa ctggatctca acagcggtaa gatccttgag agttttcgcc     1980
ccgaagaacg ttttccaatg atgagcactt taaagttct gctatgtggc gcggtattat     2040
cccgtattga cgccgggcaa gagcaactcg gtcgccgcat acactattct cagaatgact     2100
tggttgagta ctcaccagtc acagaaaagc atcttacgga tggcatgaca gtaagagaat     2160
tatgcagtgc tgccataacc atgagtgata acactgcggc caacttactt ctgacaacga     2220
tcggaggacc gaaggagcta accgcttttt tgcacaacat ggggatcat gtaactcgcc     2280
ttgatcgttg ggaaccggag ctgaatgaag ccataccaaa cgacgagcgt gacaccacga     2340
tgcctgtagc aatggcaaca acgttgcgca aactattaac tggcgaacta cttactctag     2400
cttcccggca acaattaata gactggatgg aggcggataa agttgcagga ccacttctgc     2460
gctcggccct tccggctggc tggtttattg ctgataaatc tggagccggt gagcgtgggt     2520
ctcgcggtat cattgcagca ctggggccag atggtaagcc ctcccgtatc gtagttatct     2580
acacgacggg gagtcaggca actatggatg aacgaaatag acagatcgct gagataggtg     2640
cctcactgat taagcattgg taactgtcag accaagttta ctcatatata ctttagattg     2700
atttaaaact catttttaa tttaaaagga tctaggtgaa gatcctttt gataatctca     2760
tgaccaaaat cccttaacgt gagttttcgt tccactgagc gtcagacccc gtagaaaaga     2820
tcaaaggatc ttcttgagat cctttttttc tgcgcgtaat ctgctgcttg caaacaaaaa     2880
aaccaccgct accagcggtg gtttgtttgc cggatcaaga gctaccaact cttttttccga     2940
aggtaactgg cttcagcaga gcgcagatac caaatactgt tcttctagtg tagccgtagt     3000
taggccacca cttcaagaac tctgtagcac cgcctacata cctcgctctg ctaatcctgt     3060
taccagtggc tgctgccagt ggcgataagt cgtgtcttac cgggttggac tcaagacgat     3120
```

```
agttaccgga taaggcgcag cggtcgggct gaacgggggg ttcgtgcaca cagcccagct    3180
tggagcgaac gacctacacc gaactgagat acctacagcg tgagctatga aaagcgcca     3240 cgcttcccga agggagaaag gcggacaggt atccggtaag cggcagggtc ggaacaggag    3300
agcgcacgag ggagcttcca gggggaaacg cctggtatct ttatagtcct gtcgggtttc    3360
gccacctctg acttgagcgt cgattttttgt gatgctcgtc agggggggcgg agcctatgga  3420 aaaacgccag caacgcggcc ttttttacggt tcctggcctt ttgctggcct tttgctcaca    3480
tgttctttcc tgcgttatcc cctgattctg tggataaccg tattaccgcc tttgagtgag    3540
ctgataccgc tcgccgcagc cgaacgaccg agcgcagcga gtcagtgagc gaggaagcgg    3600
aagagcgccc aatacgcaaa ccgcctctcc ccgcgcgttg gccgattcat taatgcagct    3660
ggcacgacag gtttcccgac tggaaagcgg gcagtgagcg caacgcaatt aatgtgagtt    3720
agctcactca ttaggcaccc caggctttac actttatgct tccggctcgt atgttgtgtg    3780
gaattgtgag cggataacaa tttcacacag gaaacagcta tgaccatgat tacgccagat    3840
ttaattaagg ccttaattag gctgcgcgct cgctcgctca ctgaggccgc ccgggcaaag    3900
cccgggcgtc gggcgacctt tggtcgcccg gcctcagtga gcgagcgagc gcgcagagag    3960
ggagtggcca actccatcac tagggggttcc ttgtagttaa tgattaaccc gccatgctac    4020
ttatctacca gggtaatggg gatcctctag aactatagct agtcgacatt gattattgac     4080
tagttattaa tagtaatcaa ttacggggtc attagttcat agcccatata tggagttccg     4140
cgttacataa cttacggtaa atggcccgcc tggctgaccg cccaacgacc cccgcccatt    4200
gacgtcaata atgacgtatg ttcccatagt aacgccaata gggactttcc attgacgtca    4260
atgggtggac tatttacggt aaactgccca cttggcagta catcaagtgt atcatatgcc    4320
aagtacgccc cctattgacg tcaatgacgg taaatggccc gcctggcatt atgcccagta    4380
catgacctta tgggactttc ctacttggca gtacatctac gtattagtca tcgctattac    4440
catggtcgag gtgagcccca cgttctgctt cactctcccc atctcccccc cctccccacc    4500
cccaattttg tatttattta ttttttaatt attttgtgca gcgatggggg cggggggggg    4560
gggggggcgc gcgccaggcg ggggcggggcg gggcgagggg cggggcgggg cgaggcggag    4620
aggtgcggcg gcagccaatc agagcggcgc gctccgaaag tttccttttta tggcgaggcg    4680 gcggcggcg cggccctata aaagcgaagg cgcgcggcgg gcggggagtc gctgcgacgc     4740
tgccttcgcc ccgtgccccg ctccgccgcc gcctcgcgcc gcccgccccg gctctgactg    4800
accgcgttac tcccacaggt gagcgggcgg gacggccctt ctcctccggg ctgtaattag    4860
cgcttggttt aatgacggct tgtttctttt ctgtggctgc gtgaaagcct tgaggggctc    4920
cgggagggcc ctttgtgcgg ggggagcggc tcgggggggtg cgtgcgtgtg tgtgtgcgtg    4980
gggagcgccg cgtgcggctc cgcgctgccc ggcggctgtg agcgctgcgg gcgcggcgcg    5040
gggctttgtg cgctccgcag tgtgcgcgag gggagcgcgg ccggggggcgg tgccccgcgg   5100 tgcgggggggg gctgcgaggg gaacaaaggc tgcgtgcggg gtgtgtgcgt ggggggggtga  5160 gcagggggtg tgggcgcgtc ggtcgggctg caaccccccc tgcaccccccc tcccgagtt    5220 gctgagcacg gccccggcttc gggtgcgggg ctccgtacgg ggcgtggcgc ggggctcgcc    5280
gtgccgggcg gggggtggcg gcaggtgggg gtgccgggcg gggcggggcc gcctcgggcc    5340
ggggagggct cggggggaggg gcgcggccggc cccccggagcg ccggcggctg tcgaggcgcg    5400
gcgagccgca gccattgcct tttatggtaa tcgtgcgaga gggcgcaggg acttcctttg    5460
```

| | | | | |
|---|---|---|---|---|
| tcccaaatct | gtgcggagcc | gaaatctggg | aggcgccgcc | gcaccccctc tagcgggcgc | 5520 |
| ggggcgaagc | ggtgcggcgc | cggcaggaag | gaaatgggcg | gggagggcct tcgtgcgtcg | 5580 |
| ccgcgccgcc | gtccccttct | ccctctccag | cctcggggct | gtccgcgggg ggacggctgc | 5640 |
| cttcggggg | gacggggcag | ggcggggttc | ggcttctggc | gtgtgaccgg cggctctaga | 5700 |
| gcctctgcta | accatgttca | tgccttcttc | tttttcctac | agctcctggg caacgtgctg | 5760 |
| gttattgtgc | tgtctcatca | ttttggcaaa | g | | 5791 |

```
<210> SEQ ID NO 2
<211> LENGTH: 5749
<212> TYPE: DNA
<213> ORGANISM: Artificial Sequence
<220> FEATURE:
<223> OTHER INFORMATION: constructed sequence
<220> FEATURE:
<221> NAME/KEY: polyA_signal
<222> LOCATION: (56)..(182)
<223> OTHER INFORMATION: Rabbit\globin\poly\A
<220> FEATURE:
<221> NAME/KEY: repeat_region
<222> LOCATION: (271)..(400)
<223> OTHER INFORMATION: 3' ITR (complement)
<220> FEATURE:
<221> NAME/KEY: rep_origin
<222> LOCATION: (577)..(1032)
<223> OTHER INFORMATION: F1 ori
<220> FEATURE:
<221> NAME/KEY: misc_feature
<222> LOCATION: (1163)..(2020)
<223> OTHER INFORMATION: AP(R)
<220> FEATURE:
<221> NAME/KEY: rep_origin
<222> LOCATION: (2194)..(2782)
<223> OTHER INFORMATION: Origin\of\replication
<220> FEATURE:
<221> NAME/KEY: repeat_region
<222> LOCATION: (3222)..(3351)
<223> OTHER INFORMATION: 5' ITR
<220> FEATURE:
<221> NAME/KEY: repeat_region
<222> LOCATION: (3419)..(3800)
<223> OTHER INFORMATION: CMV\IE\promoter
<220> FEATURE:
<221> NAME/KEY: promoter
<222> LOCATION: (3803)..(4084)
<223> OTHER INFORMATION: CB promoter
<220> FEATURE:
<221> NAME/KEY: TATA_signal
<222> LOCATION: (4057)..(4060)
<220> FEATURE:
<221> NAME/KEY: Intron
<222> LOCATION: (4179)..(5151)
<223> OTHER INFORMATION: chicken\beta-actin\intron
<220> FEATURE:
<221> NAME/KEY: misc_feature
<222> LOCATION: (5163)..(5738)
<223> OTHER INFORMATION: Epo

<400> SEQUENCE: 2
```

| | | | | |
|---|---|---|---|---|
| ctctagagtc | gacccgggcg | gcctcgagga | cggggtgaac | tacgcctgag gatccgatct | 60 |
| ttttccctct | gccaaaaatt | atggggacat | catgaagccc | cttgagcatc tgacttctgg | 120 |
| ctaataaagg | aaatttattt | tcattgcaat | agtgtgttgg | aattttttgt gtctctcact | 180 |
| cggaagcaat | tcgttgatct | gaatttcgac | cacccataat | acccattacc ctggtagata | 240 |
| agtagcatgg | cgggttaatc | attaactaca | aggaacccct | agtgatggag ttggccactc | 300 |
| cctctctgcg | cgctcgctcg | ctcactgagg | ccgggcgacc | aaaggtcgcc cgacgcccgg | 360 |
| gctttgcccg | ggcggcctca | gtgagcgagc | gagcgcgcag | ccttaattaa cctaattcac | 420 |

```
tggccgtcgt tttacaacgt cgtgactggg aaaaccctgg cgttacccaa cttaatcgcc    480
ttgcagcaca tccccctttc gccagctggc gtaatagcga agaggcccgc accgatcgcc    540
cttcccaaca gttgcgcagc ctgaatggcg aatgggacgc gccctgtagc ggcgcattaa    600
gcgcggcggg tgtggtggtt acgcgcagcg tgaccgctac acttgccagc gccctagcgc    660
ccgctccttt cgctttcttc ccttcctttc tcgccacgtt cgccggcttt ccccgtcaag    720
ctctaaatcg ggggctccct ttagggttcc gatttagtgc tttacggcac ctcgacccca    780
aaaaacttga ttagggtgat ggttcacgta gtgggccatc gccctgatag acggtttttc    840
gccctttgac gttggagtcc acgttcttta atagtggact cttgttccaa actggaacaa    900
cactcaaccc tatctcggtc tattcttttg atttataagg gattttgccg atttcggcct    960
attggttaaa aaatgagctg atttaacaaa aatttaacgc gaattttaac aaaatattaa    1020
cgcttacaat ttaggtggca cttttcgggg aaatgtgcgc ggaaccccta tttgtttatt    1080
tttctaaata cattcaaata tgtatccgct catgagacaa taaccctgat aaatgcttca    1140
ataatattga aaaggaaga gtatgagtat tcaacatttc cgtgtcgccc ttattccctt    1200
ttttgcggca ttttgccttc ctgttttgc tcacccagaa acgctggtga agtaaaaga    1260 tgctgaagat cagttgggtg cacgagtggg ttacatcgaa ctggatctca acagcggtaa    1320
gatccttgag agttttcgcc ccgaagaacg ttttccaatg atgagcactt ttaaagttct    1380
gctatgtggc gcggtattat cccgtattga cgccgggcaa gagcaactcg gtcgccgcat    1440
acactattct cagaatgact tggttgagta ctcaccagtc acagaaaagc atcttacgga    1500
tggcatgaca gtaagagaat tatgcagtgc tgccataacc atgagtgata acactgcggc    1560
caacttactt ctgacaacga tcggaggacc gaaggagcta accgcttttt tgcacaacat    1620
gggggatcat gtaactcgcc ttgatcgttg ggaaccggag ctgaatgaag ccataccaaa    1680
cgacgagcgt gacaccacga tgcctgtagc aatggcaaca acgttgcgca aactattaac    1740
tggcgaacta cttactctag cttcccggca acaattaata gactggatgg aggcggataa    1800
agttgcagga ccacttctgc gctcggccct tccggctggc tggtttattg ctgataaatc    1860
tggagccggt gagcgtgggt ctcgcggtat cattgcagca ctggggccag atggtaagcc    1920
ctcccgtatc gtagttatct acacgacggg gagtcaggca actatggatg aacgaaatag    1980
acagatcgct gagataggtg cctcactgat taagcattgg taactgtcag accaagttta    2040
ctcatatata ctttagattg atttaaaact tcatttttaa tttaaaagga tctaggtgaa    2100 gatcctttt gataatctca tgaccaaaat cccttaacgt gagttttcgt tccactgagc    2160
gtcagacccc gtagaaaaga tcaaaggatc ttcttgagat cctttttttc tgcgcgtaat    2220
ctgctgcttg caaacaaaaa aaccaccgct accagcggtg gtttgtttgc cggatcaaga    2280
gctaccaact ctttttccga aggtaactgg cttcagcaga gcgcagatac caaatactgt    2340
tcttctagtg tagccgtagt taggccacca cttcaagaac tctgtagcac cgcctacata    2400
cctcgctctg ctaatcctgt taccagtggc tgctgccagt ggcgataagt cgtgtcttac    2460
cgggttggac tcaagacgat agttaccgga taaggcgcag cggtcgggct gaacggggg    2520 ttcgtgcaca cagcccagct tggagcgaac gacctacacc gaactgagat acctacagcg    2580
tgagctatga gaaagcgcca cgcttcccga agggagaaag gcggacaggt atccggtaag    2640
cggcagggtc ggaacaggag agcgcacgag ggagcttcca gggggaaacg cctggtatct    2700
ttatagtcct gtcgggtttc gccacctctg acttgagcgt cgatttttgt gatgctcgtc    2760 agggggggcgg agcctatgga aaaacgccag caacgcggcc ttttttacggt tcctggcctt    2820
```

```
ttgctggcct tttgctcaca tgttctttcc tgcgttatcc cctgattctg tggataaccg    2880
tattaccgcc tttgagtgag ctgataccgc tcgccgcagc cgaacgaccg agcgcagcga    2940
gtcagtgagc gaggaagcgg aagagcgccc aatacgcaaa ccgcctctcc ccgcgcgttg    3000
gccgattcat taatgcagct ggcacgacag gtttcccgac tggaaagcgg gcagtgagcg    3060
caacgcaatt aatgtgagtt agctcactca ttaggcaccc caggctttac actttatgct    3120
tccggctcgt atgttgtgtg gaattgtgag cggataacaa tttcacacag gaaacagcta    3180
tgaccatgat tacgccagat ttaattaagg ccttaattag gctgcgcgct cgctcgctca    3240
ctgaggccgc ccgggcaaag cccgggcgtc gggcgacctt tggtcgcccg gcctcagtga    3300
gcgagcgagc gcgcagagag ggagtggcca actccatcac taggggttcc ttgtagttaa    3360
tgattaaccc gccatgctac ttatctacca gggtaatggg gatcctctag aactatagct    3420
agtcgacatt gattattgac tagttattaa tagtaatcaa ttacggggtc attagttcat    3480
agcccatata tggagttccg cgttacataa cttacggtaa atggcccgcc tggctgaccg    3540
cccaacgacc cccgcccatt gacgtcaata atgacgtatg ttcccatagt aacgccaata    3600
gggactttcc attgacgtca atgggtggac tatttacggt aaactgccca cttggcagta    3660
catcaagtgt atcatatgcc aagtacgccc cctattgacg tcaatgacgg taaatggccc    3720
gcctggcatt atgcccagta catgacctta tgggactttc ctacttggca gtacatctac    3780
gtattagtca tcgctattac catggtcgag gtgagcccca cgttctgctt cactctcccc    3840
atctcccccc cctccccacc cccaattttg tatttattta ttttttaatt attttgtgca    3900
gcgatggggg cggggggggg gggggggcgc gcgccaggcg gggcggggcg gggcgagggg    3960
cggggcgggg cgaggcggag aggtgcggcg gcagccaatc agagcggcgc gctccgaaag    4020
tttccttttg tggcgaggcg gcggcggcgg cggccctata aaaagcgaag cgcgcggcgg    4080
gcggggagtc gctgcgacgc tgccttcgcc ccgtgccccg ctccgccgcc gcctcgcgcc    4140
gcccgccccg gctctgactg accgcgttac tcccacaggt gagcgggcgg gacggccctt    4200
ctcctccggg ctgtaattag cgcttggttt aatgacggct tgtttctttt ctgtggctgc    4260
gtgaaagcct tgaggggctc cgggagggcc ctttgtgcgg gggagcggc tcgggggtg     4320
cgtgcgtgtg tgtgtgcgtg gggagcgccg cgtgcggctc cgcgctgccc ggcggctgtg    4380
agcgctgcgg gcgcggcgcg gggctttgtg cgctccgcag tgtgcgcgag gggagcgcgg    4440
ccggggcgg tgccccgcgg tgcggggggg gctgcgaggg gaacaaaggc tgcgtgcggg     4500
gtgtgtgcgt ggggggggtga gcaggggtg tgggcgcgtc ggtcgggctg caacccccccc    4560
tgcaccccc tccccgagtt gctgagcacg gcccggcttc gggtgcgggg ctccgtacgg     4620
ggcgtggcgc gggctcgcc gtgccggggcg ggggtggcg gcaggtgggg gtgccgggcg     4680
gggcggggcc gcctcgggcc ggggagggct cggggagg gcgcggcggc cccggagcg       4740
ccggcggctg tcgaggcgcg gcgagccgca gccattgcct tttatggtaa tcgtgcgaga    4800
gggcgcaggg acttcctttg tcccaaatct gtgcggagcc gaaatctggg aggcgccgcc    4860
gcacccctc tagcgggcgc ggggcgaagc ggtgcggcgc cggcaggaag gaaatgggcg    4920
gggagggcct tcgtgcgtcg ccgcgccgcc gtccccttct ccctctccag cctcggggct    4980
gtccgcgggg ggacggctgc cttcgggggg gacggggcag ggcggggttc ggcttctggc    5040
gtgtgaccgg cggctctaga gcctctgcta accatgttca tgccttcttc ttttttcctac   5100
agctcctggg caacgtgctg gttattgtgc tgtctcatca ttttggcaaa gaattcgcca    5160
```

-continued

```
ccatgggcag ctgcgagtgt cctgctctcc tgctgctgct gagtttgctg ctgctgcctc   5220
tgggcctgcc tgtgctggga gcacctccta gactgatctg cgacagccgg gtgctggaac   5280
ggtacatcct ggaagcccgc gaggccgaga atgtgaccat gggatgtgcc gagggctgca   5340
gcttcagcga gaacatcacc gtgcccgaca ccaaagtgaa cttctacacc tggaagagaa   5400
tggacgtggg ccagcaggcc gtggaagtgt ggcagggact ggccctgctg tctgaggcca   5460
tcctgagagg acaggctctg ctggccaaca gcagccagcc tagcgaaacc ctgcagctgc   5520
acgtggacaa ggccgtgtcc tccctgagaa gcctgaccag cctgctgaga gcactgggag   5580
cccagaaaga ggccacctct ctgcctgagg ccacatctgc cgcccctctg agaaccttca   5640
ccgtggacac cctgtgcaag ctgttccgga tctacagcaa cttcctgcgg ggcaagctga   5700
ccctgtacac cggcgaggct tgtcggagag gcgacagatg atgaggtac              5749
```

```

<210> SEQ ID NO 3
<211> LENGTH: 206
<212> TYPE: PRT
<213> ORGANISM: Canis familiaris

<400> SEQUENCE: 3

Met Cys Glu Pro Ala Pro Pro Lys Pro Thr Gln Ser Ala Trp His Ser
1               5                   10                  15

Phe Pro Glu Cys Pro Ala Leu Leu Leu Leu Leu Ser Leu Leu Leu Leu
            20                  25                  30

Pro Leu Gly Leu Pro Val Leu Gly Ala Pro Pro Arg Leu Ile Cys Asp
        35                  40                  45

Ser Arg Val Leu Glu Arg Tyr Ile Leu Glu Ala Arg Glu Ala Glu Asn
    50                  55                  60

Val Thr Met Gly Cys Ala Gln Gly Cys Ser Phe Ser Glu Asn Ile Thr
65                  70                  75                  80

Val Pro Asp Thr Lys Val Asn Phe Tyr Thr Trp Lys Arg Met Asp Val
                85                  90                  95

Gly Gln Gln Ala Leu Glu Val Trp Gln Gly Leu Ala Leu Leu Ser Glu
            100                 105                 110

Ala Ile Leu Arg Gly Gln Ala Leu Leu Ala Asn Ala Ser Gln Pro Ser
        115                 120                 125

Glu Thr Pro Gln Leu His Val Asp Lys Ala Val Ser Ser Leu Arg Ser
    130                 135                 140

Leu Thr Ser Leu Leu Arg Ala Leu Gly Ala Gln Lys Glu Ala Met Ser
145                 150                 155                 160

Leu Pro Glu Glu Ala Ser Pro Ala Pro Leu Arg Thr Phe Thr Val Asp
                165                 170                 175

Thr Leu Cys Lys Leu Phe Arg Ile Tyr Ser Asn Phe Leu Arg Gly Lys
            180                 185                 190

Leu Thr Leu Tyr Thr Gly Glu Ala Cys Arg Arg Gly Asp Arg
        195                 200                 205

<210> SEQ ID NO 4
<211> LENGTH: 192
<212> TYPE: PRT
<213> ORGANISM: Felis catus

<400> SEQUENCE: 4

Met Gly Ser Cys Glu Cys Pro Ala Leu Leu Leu Leu Leu Ser Leu Leu
1               5                   10                  15
```

Leu Leu Pro Leu Gly Leu Pro Val Leu Gly Ala Pro Pro Arg Leu Ile
            20                  25                  30

Cys Asp Ser Arg Val Leu Glu Arg Tyr Ile Leu Glu Ala Arg Glu Ala
            35                  40                  45

Glu Asn Val Thr Met Gly Cys Ala Glu Gly Cys Ser Phe Ser Glu Asn
        50                  55                  60

Ile Thr Val Pro Asp Thr Lys Val Asn Phe Tyr Thr Trp Lys Arg Met
65                  70                  75                  80

Asp Val Gly Gln Gln Ala Val Glu Val Trp Gln Gly Leu Ala Leu Leu
                85                  90                  95

Ser Glu Ala Ile Leu Arg Gly Gln Ala Leu Leu Ala Asn Ser Ser Gln
            100                 105                 110

Pro Ser Glu Thr Leu Gln Leu His Val Asp Lys Ala Val Ser Ser Leu
        115                 120                 125

Arg Ser Leu Thr Ser Leu Leu Arg Ala Leu Gly Ala Gln Lys Glu Ala
    130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
                165                 170                 175

Gly Lys Leu Thr Leu Tyr Thr Gly Glu Ala Cys Arg Arg Gly Asp Arg
            180                 185                 190

<210> SEQ ID NO 5
<211> LENGTH: 576
<212> TYPE: DNA
<213> ORGANISM: Canis familiaris

<400> SEQUENCE: 5
atgggggcgt gcgaatgtcc tgccctgttc cttttgctgt ctttgctgct gcttcctctg      60
ggcctcccag tcctgggcgc ccccctcgc ctcatttgtg acagccgggt cctggagaga     120
tacatcctgg aggccaggga ggccgaaaat gtcacgatgg gctgtgctca aggctgcagc     180
ttcagtgaga atatcaccgt cccagacacc aaggttaatt tctatacctg gaagaggatg     240
gatgttgggc agcaggcctt ggaagtctgg cagggcctgg cactgctctc agaagccatc     300
ctgcggggtc aggccctgtt ggccaacgcc tcccagccat ctgagactcc gcagctgcat     360
gtggacaaag ccgtcagcag cctgcgcagc ctcacctctc tgcttcgggc gctgggagcc     420
cagaaggagg ccatgtccct tccagaggaa gcctctcctg ctccactccg aacattcact     480
gttgatactt tgtgcaaact tttccgaatc tactccaatt tcctccgtgg aaagctgaca     540
ctgtacacag gggaggcctg cagaagagga gacagg                               576

<210> SEQ ID NO 6
<211> LENGTH: 579
<212> TYPE: DNA
<213> ORGANISM: Felis catus

<400> SEQUENCE: 6
atggggtcgt gcgaatgtcc tgccctgctg cttctgctat ctttgctgct gcttccctg      60 ggcctcccag tcctgggcgc ccccctcgc ctcatctgtg acagccgagt cctggagagg     120
tacattctgg gggccaggga ggccgaaaat gtcacgatgg gctgtgctga aggctgcagc     180
ttcagtgaga atatcactgt cccagacacc aaggtcaact tctatacctg gaagaggatg     240
gacgtcgggc agcaggctgt ggaagtctgg cagggcctcg ccctgctctc agaagccatc     300

```
ctgcggggcc aggccctgct ggccaactcc tcccagccat ctgagaccct gcagctgcat    360
gtggataaag ccgtcagcag cctgcgcagc ctcacctccc tgcttcgggc actgggagcc    420
cagaaggaag ccacctccct tccagaggca acctctgctg ctccactccg aacattcact    480
gtcgatactt tgtgcaaact tttccgaatc tactccaact tcctgcgggg aaagctgacg    540
ctgtacacag gggaggcctg ccgaagagga gacaggtga                           579
```

<210> SEQ ID NO 7
<211> LENGTH: 618
<212> TYPE: DNA
<213> ORGANISM: Artificial Sequence
<220> FEATURE:
<223> OTHER INFORMATION: codon optimized sequence

<400> SEQUENCE: 7

```
atgtgcgagc ctgccccccc taagcctaca cagtctgcct ggcacagctt ccccgagtgt     60
cctgctctcc tgctgctgct gagtttgctg ctgctgcctc tgggcctgcc tgtgctggga    120
gcacctccta gactgatctg cgacagccgg gtgctggaac ggtacatcct ggaagcccgc    180
gaggccgaga atgtgaccat gggatgtgcc cagggctgca gcttcagcga gaacatcacc    240
gtgcccgaca ccaaagtgaa cttctacacc tggaagagaa tggacgtggg ccagcaggcc    300
ctggaagtgt ggcagggact ggccctgctg tctgaggcca tcctgagagg acaggctctg    360
ctggccaatg ccagccagcc tagcgagaca cctcagctgc acgtggacaa ggccgtgtcc    420
tccctgagaa gcctgaccag cctgctgaga gcactgggag cccagaaaga agccatgagc    480
ctgcctgagg aagccagccc tgcccctctg agaaccttca ccgtggacac cctgtgcaag    540
ctgttccgga tctacagcaa cttcctgcgg ggcaagctga ccctgtacac cggcgaggct    600
tgtcggagag gcgacaga                                                  618
```

<210> SEQ ID NO 8
<211> LENGTH: 576
<212> TYPE: DNA
<213> ORGANISM: Artificial Sequence
<220> FEATURE:
<223> OTHER INFORMATION: codon optimized sequence

<400> SEQUENCE: 8

```
atgggcagct gcgagtgtcc tgctctcctg ctgctgctga gtttgctgct gctgcctctg     60
ggcctgcctg tgctgggagc acctcctaga ctgatctgcg acagccgggt gctggaacgg    120
tacatcctgg aagcccgcga ggccgagaat gtgaccatgg gatgtgccga gggctgcagc    180
ttcagcgaga acatcaccgt gcccgacacc aaagtgaact tctacacctg gaagagaatg    240
gacgtgggcc agcaggccgt ggaagtgtgg cagggactgg ccctgctgtc tgaggccatc    300
ctgagaggac aggctctgct ggccaacagc agccagccta gcgaaaccct gcagctgcac    360
gtggacaagg ccgtgtcctc cctgagaagc ctgaccagcc tgctgagagc actgggagcc    420
cagaaagagg ccacctctct gcctgaggcc acatctgccg cccctctgag aaccttcacc    480
gtggacaccc tgtgcaagct gttccggatc tacagcaact cctgcggggc aagctgacc    540 ctgtacaccg gcgaggcttg tcggagaggc gacaga                              576
```

<210> SEQ ID NO 9
<211> LENGTH: 20
<212> TYPE: PRT
<213> ORGANISM: Artificial Sequence
<220> FEATURE:

```
<223> OTHER INFORMATION: IL-2 leader

<400> SEQUENCE: 9

Met Tyr Arg Met Gln Leu Leu Ser Cys Ile Ala Leu Ser Leu Ala Leu
1               5                   10                  15

Val Thr Asn Ser
            20
```

AAV-EPO FOR TREATING COMPANION ANIMALS

INCORPORATION-BY-REFERENCE OF MATERIAL SUBMITTED IN ELECTRONIC FORM

Applicant hereby incorporates by reference the Sequence Listing material filed in electronic form herewith. This file is labeled "15-7472PCT_Seq_Listing.txt".

BACKGROUND OF THE INVENTION

Erythropoietin (EPO) is a hormone made predominantly within the peritubular cells of the kidney. It acts on the bone marrow, stimulating erythropoiesis. Erythropoietin also controls apoptosis (programmed cell death) of mature red blood cells. Renal disease reduces erythropoietin production. In humans, the management of anemia in chronic kidney disease has been revolutionized by the development of recombinant human erythropoietin (epoetin). Many of the symptoms that had been ascribed to chronic kidney disease such as fatigue, lethargy, somnolence and shortness of breath, which all impact unfavorably on quality of life, were resolved or markedly improved when anemia was corrected.

There are over 2 million cats and 350,000 dogs that suffer from chronic kidney disease (CKD). Companion animals with CKD-related renal failure suffer in similar ways. They do not have sufficient EPO and subsequently become very anemic. In the past veterinarians have given human recombinant EPO until the animals would develop an immune response to the infused EPO. Effectively, this leaves no long term treatment in the market for a very well understood physiological process that has a clear need in the clinic.

Therefore, compositions useful for expressing EPO in subjects, particularly companion animals, are needed.

SUMMARY OF THE INVENTION

Novel engineered erythropoietin (EPO) constructs are provided herein. These constructs can be delivered to subjects in need thereof via a number of routes, and particularly by expression in vivo mediated by a recombinant vector such as a recombinant adeno-associated virus (rAAV) vector.

In some embodiments, the EPO is encoded by an endogenous sequence. That is, the EPO sequence is derived from the same subject species for which administration is ultimately intended.

In some embodiments, a pharmaceutical composition comprising a pharmaceutically acceptable carrier and a recombinant vector as described herein is provided. Also provided are methods for treating chronic kidney disease by administering to a subject in need thereof a recombinant vector described herein that has an expression cassette, wherein said expression cassette further comprises regulatory control sequences which direct expression of the EPO construct in the subject. In some embodiments, the subject being treated is a companion animal. In one embodiment, the subject is a feline. In another embodiment, the subject is a canine. As used herein, the terms "patient" and "subject" are used interchangeably, and can refer to a human or veterinary subject.

In yet another embodiment, methods for increasing the amount of circulating EPO in a subject comprising providing a recombinant vector described herein that has an expression cassette encoding EPO.

The recombinant vectors described above can be used in a regimen for treating chronic kidney disease and other conditions characterized by a decrease in the amount of circulating red blood cells.

Other aspects and advantages of the invention will be readily apparent from the following detailed description of the invention.

BRIEF DESCRIPTION OF THE DRAWINGS

FIG. 3A shows the canine EPO propeptide sequence, with the leader sequence underlined. FIG. 3B shows the feline EPO propeptide sequence, with the leader sequence underlined.

DETAILED DESCRIPTION OF THE INVENTION

Figure 1:
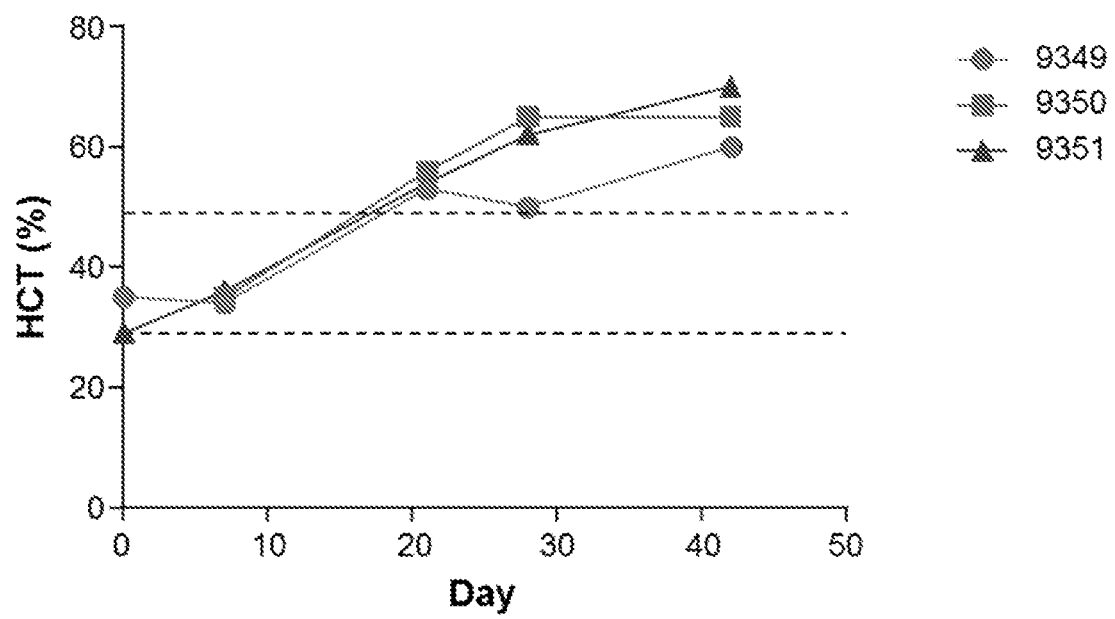
FIG. 1 is a graph showing hematocrits of cats treated with AAV8 expressing feline erythropoietin. Dashed lines indicate the normal range.

Adeno-associated viral vectors carrying EPO expression constructs have been developed for use in subjects including companion animals (e.g., feline and canine). Though likely effective, a recombinant canine or feline specific EPO protein therapeutic would cost much more to develop and manufacture than a viral vector mediated system for delivery of EPO to the affected animal. With a viral vector therapeutic, there is also the convenience of being able to treat the animal once, as opposed to frequent injections of recombinant EPO. Stable expression of EPO would correct anemia and give the animal an improved quality of life. The EPO constructs described herein are also characterized in that they provide an EPO sequence which is endogenous to the subject, which reduces the risk of the subject developing an immune response to a non-native protein.

Also provided are uses for the constructs described herein. Delivery of these constructs to subjects in need thereof via a number of routes, and particularly for expression in vivo which is mediated by a recombinant vector such as a rAAV vector, is described. In one embodiment, methods of using the constructs in regimens for treating chronic kidney disease in a subject in need thereof and increasing the EPO in a subject are also provided. In one embodiment, methods of using these constructs in regimens for treating anemia in a subject in need thereof are provided. In another embodiment, the subject's anemia is related to the use of other medications. Possible medications which contribute to anemia include, but are not limited to, HIV/AIDS treatments (including AZT) and cancer therapeutics, including chemotherapy. In another embodiment, the subject's anemia is related to a medical condition. Possible medical conditions that contribute to anemia include, but are not limited to, cancer, HIV/AIDS, rheumatoid arthritis, Crohn's disease and other chronic inflammatory diseases and dysfunctional bone marrow (e.g., aplastic anemia, leukemia, myelodysplasia or myelofibrosis), multiple myeloma, myeloproliferative disorders and lymphoma, hemolytic anemia, sickle cell anemia and thalassemia. In addition, methods are provided for enhancing the activity of EPO in a subject.

EPO is expressed in vivo as a propeptide, with the leader sequences sharing some homology across species. SEQ ID NO: 3 shows the sequence of the canine EPO propeptide, with the mature protein beginning at amino acid 41. The leader sequence is underlined in FIG. 3a. SEQ ID NO: 4 shows the sequence of the feline EPO propeptide, with the mature protein beginning at amino acid 27. The leader sequence is underlined in FIG. 3B.

In one embodiment, functional variants of EPO include variants which may include up to about 10% variation from an EPO nucleic acid or amino acid sequence described herein or known in the art, which retain the function of the wild type sequence. The sequence on which the EPO variant is based may, in some embodiments, include the propeptide leader sequence (e.g., as shown in SEQ ID NO: 3 and SEQ ID NO: 4). In another embodiment, the EPO variant described herein refers only to the mature peptide (e.g., amino acids 41-206 of SEQ ID NO: 3 or amino acids 27-192 of SEQ ID NO: 4). As used herein, by "retain function" it is meant that the nucleic acid or amino acid functions in the same way as the wild type sequence, although not necessarily at the same level of expression or activity. For example, in one embodiment, a functional variant has increased expression or activity as compared to the wild type sequence. In another embodiment, the functional variant has decreased expression or activity as compared to the wild type sequence. In one embodiment, the functional variant has 10%, 20%, 30%, 40%, 50%, 60%, 70%, 80%, 90% or greater increase or decrease in expression or activity as compared to the wild type sequence. The amino acid sequence of canine EPO is provided herein as SEQ ID NO: 3. The amino acid sequence of feline EPO is provided herein as SEQ ID NO: 4.

In another embodiment, functional variants of EPO include variants which may include up to about 20% variation from an EPO nucleic acid or amino acid sequence described herein or known in the art, which retain the function of the wild type sequence. In one embodiment, functional variants of EPO include variants which may include up to about 30% variation from an EPO nucleic acid or amino acid sequence described herein or known in the art, which retain the function of the wild type sequence. The following alignment shows the canine sequence on top, the feline sequence on the bottom, with the consensus sequence in the middle.

substitutions are made in a residue in which variation is shown across species as in the alignment above. In another embodiment, one or more amino acid substitutions are made in a residue in which conservation is shown across species. Although EPO shares a high degree of identity across species, in one embodiment, it is desirable to select the EPO sequence based on the species of the subject for which administration of the vector is ultimately intended. In one example, the subject is a mammal. For example, in one embodiment, if the subject is a feline, the EPO sequence is derived from a feline protein. In another embodiment, the EPO sequence is derived from a canine protein. In another embodiment, the EPO sequence is derived from a non-human primate protein. In another embodiment, the EPO is derived from bovine, ovine, or porcine protein. In another embodiment, the EPO sequence is SEQ ID NO: 3. In another embodiment, the EPO sequence is SEQ ID NO: 4.

The EPO peptide or nucleic acid coding sequence may include a heterologous leader sequence in conjunction with the EPO mature protein sequence. The term "heterologous" when used with reference to a protein or a nucleic acid indicates that the protein or the nucleic acid comprises two or more sequences or subsequences which are not found in the same relationship to each other in nature. For instance, the expression cassette is typically recombinantly produced, having two or more sequences from unrelated genes arranged to make a new functional nucleic acid. For example, in one embodiment, the leader sequence may be from a different gene than EPO. Thus, with reference to the EPO coding sequences, the leader is heterologous. In one embodiment, the leader sequence is derived from a different species than the EPO sequence.

In one embodiment, the sequence encodes an IL-2 leader peptide fused upstream of the EPO mature polypeptide. In one embodiment, the leader sequence is SEQ ID NO: 9: M Y R M Q L L S C I A L S L A L V T N S. However, another heterologous leader sequence may be substituted for the IL-2 signal/leader peptide. The leader may be a signal sequence which is natively found in a cytokine (e.g., IL-2, IL12, IL18, or the like), immunoglobulin, insulin, albumin, β-glucuronidase, alkaline protease or the fibronectin secretory signal peptides, or sequences from tissue specific secreted proteins, amongst others. In one embodiment, the leader sequence is the endogenous leader sequence from the EPO propeptide.

```
Canine (query; amino acids 19 to 206 of SEQ ID NO: 3) v. Feline (subject,
amino acids 5 to 192 of SEQ ID NO: 4)
Query       19  ECPALLLLLSLLLLPLGLPVLGAPPRLICDSRVLERYILEAREAENVTMGCAQGCSFSEN        78
                ECPALLLLLSLLLLPLGLPVLGAPPRLICDSRVLERYILEAREAENVTMGCA+GCSFSEN
Sbjct        5  ECPALLLLLSLLLLPLGLPVLGAPPPRLICDSRVLERYILEAREAENVTMGCAEGCSFSEN       64

Query       79  ITVPDTKVNFYTWKRMDVGQQALEVWQGLALLSEAILRGQALLANASQPSETPQLHVDKA       136
                ITVPDTKVNFYTWKRMDVGQQA+EVWQGLALLSEAILRGQALLAN+SQPSET QLHVDKA
Sbjct       65  ITVPDTKVNFYTWKRMDVGQQAVEVWQGLALLSEAILRGQALLANSSQPSETLQLHVDKA       124

Query      139  VSSLRSLTSLLRALGAQKEAMSLPEEASPAPLRTFTVDTLCKLFRIYSNFLRGKLTLYTG       198
                VSSLRSLTSLLRALGAQKEA SLPE  S APLRTFTVDTLCKLFRIYSNFL GKLTLYTG
Sbjct      125  VSSLRSLTSLLRALGAQKEATSLPEATSAAPLRTFTVDTLCKLFRIYSNFLPGKLTLYTG       184

Query      199  EACRRGDR                                                          206
                EACRRGDR
Sbjct      185  EACRRGDR.                                                         192
```

In one embodiment, the term EPO refers to active EPO in which one or more amino acid substitutions have been made, as compared to the wild type sequence (SEQ ID NO: 3 or SEQ ID NO: 4, either sequence with or without the leader peptide). In one embodiment, one or more amino acid As used herein, the terms "derived" or "derived from" mean the sequence or protein is sourced from a specific subject species or shares the same sequence as a protein or sequence sourced from a specific subject species. For example, a propeptide sequence which is "derived from" a canine, shares the same sequence (or a variant thereof, as defined herein) as the same propeptide sequence as expressed in a canine. However, the specified nucleic acid or amino acid need not actually be sourced from a canine. Various techniques are known in the art which are able to produce a desired sequence, including mutagenesis of a similar protein (e.g., a homolog) or artificial production of a nucleic acid or amino acid sequence. The "derived" nucleic acid or amino acid retains the function of the same nucleic acid or amino acid in the species from which it is "derived", regardless of actual source of the derived sequence.

As used herein the terms "EPO construct", "EPO expression construct" and synonyms include the EPO sequence as described herein. The terms "EPO construct", "EPO expression construct" and synonyms can be used to refer to the nucleic acid sequences encoding the EPO (including the EPO mature protein or propeptide with endogenous or heterologous leader) or the expression products thereof.

The term "amino acid substitution" and its synonyms are intended to encompass modification of an amino acid sequence by replacement of an amino acid with another, substituting, amino acid. The substitution may be a conservative substitution. It may also be a non-conservative substitution. The term conservative, in referring to two amino acids, is intended to mean that the amino acids share a common property recognized by one of skill in the art. For example, amino acids having hydrophobic nonacidic side chains, amino acids having hydrophobic acidic side chains, amino acids having hydrophilic nonacidic side chains, amino acids having hydrophilic acidic side chains, and amino acids having hydrophilic basic side chains. Common properties may also be amino acids having hydrophobic side chains, amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Methods for replacing an amino acid are well known to the skilled in the art and include, but are not limited to, mutations of the nucleotide sequence encoding the amino acid sequence. Reference to "one or more" herein is intended to encompass the individual embodiments of, for example, 1, 2, 3, 4, 5, 6, or more.

Also provided are the assembled EPO proteins described herein. In one embodiment, the EPO protein is produced by a described AAV construct. In one embodiment, the EPO protein includes a heterologous leader combined with the mature EPO protein. In one embodiment, the heterologous leader is from IL-2. The assembled EPO proteins have many uses including diagnostic assays. Thus, in one embodiment, the EPO protein is labeled. As used herein, "labels" are chemical or biochemical moieties useful for labeling the EPO protein. "Labels" include fluorescent agents, chemiluminescent agents, chromogenic agents, quenching agents, radionucleotides, enzymes, substrates, cofactors, inhibitors, radioactive isotopes, magnetic particles, and other moieties known in the art. "Labels" or "reporter molecules" are capable of generating a measurable signal and may be covalently or noncovalently joined to an oligonucleotide or nucleotide (e.g., a non-natural nucleotide) or ligand. Most desirably, the label is detectable visually, e.g. colorimetrically. Many such labels are known in the art and include, without limitation, fluorescent detectable fluorochromes, e.g., fluorescein isothiocyanate (FITC), phycoerythrin (PE), allophycocyanin (APC), coriphosphine-O (CPO) or tandem dyes, PE-cyanin-5 (PC5), and PE-Texas Red (ECD). Commonly used fluorochromes include fluorescein isothiocyanate (FITC), phycoerythrin (PE), allophycocyanin (APC), and also include the tandem dyes, PE-cyanin-5 (PC5), PE-cyanin-7 (PC7), PE-cyanin-5.5, PE-Texas Red (ECD), rhodamine, PerCP, fluorescein isothiocyanate (FITC) and Alexa dyes. Combinations of such labels, such as Texas Red and rhodamine, FITC+PE, FITC+PECy5 and PE+PECy7, among others may be used depending upon assay method. Other desirable labels or tags include those which allow physical separation or immobilization on a substrate of the protein. Such labels include biotin. Other suitable labels or tags are described, e.g., in US 2011-0177967 A1, which is incorporated herein by reference.

In another embodiment, the EPO peptide includes variants which may include up to about 10% variation from the EPO sequence. That is, the EPO peptide shares about 90% identity to about 99.9% identity, about 95% to about 99% identity or about 97% to about 98% identity to the EPO sequences provided herein and/or known in the art.

In addition to the EPO peptides provided herein, nucleic acid sequences encoding these peptides are provided. In one embodiment, a nucleic acid sequence is provided which encodes for the EPO peptides described herein. In another embodiment, this includes any nucleic acid sequence which encodes the canine EPO protein of SEQ ID NO: 3 or a sequence sharing at least 90% identity with SEQ ID NO: 3. In another embodiment, this includes any nucleic acid sequence which encodes the feline EPO protein of SEQ ID NO: 4 or a sequence sharing at least 90% identity with SEQ ID NO: 4.

In one embodiment, the nucleic acid sequence encoding canine EPO is SEQ ID NO: 5. In one embodiment, the nucleic acid sequence encoding feline EPO is SEQ ID NO: 6. In yet another embodiment, the EPO nucleic acid includes variants which may include up to about 10% variation from an EPO sequence disclosed herein or known in the art. In yet another embodiment, the EPO nucleic acid includes variants which may include up to about 20% variation from an EPO sequence disclosed herein or known in the art. In yet another embodiment, the EPO nucleic acid includes variants which may include up to about 30% variation from an EPO sequence disclosed herein or known in the art. In another embodiment, the EPO nucleic acid includes variants which may include up to about 40% variation from an EPO sequence disclosed herein or known in the art.

In one embodiment, the nucleic acid sequence encoding EPO is a codon optimized sequence encoding any of the EPO peptides described herein, including sequences sharing at least 90% identity with the described sequence. In one embodiment, the nucleic acid sequence is codon optimized for expression in the subject for which administration is desired. In one embodiment, the nucleic acid sequence encoding canine EPO is SEQ ID NO: 7. In one embodiment, the nucleic acid sequence encoding feline EPO is SEQ ID NO: 8.

When a variant of the EPO peptide is desired, the coding sequences for these peptides may be generated using site-directed mutagenesis of the wild-type nucleic acid sequence. Web-based or commercially available computer programs, as well as service based companies may be used to back translate the amino acids sequences to nucleic acid coding sequences, including both RNA and/or cDNA. See, e.g., backtranseq by EMBOSS, http://www.ebi.ac.uk/Tools/st/; Gene Infinity (http://www.geneinfinity.org/sms-/sms_back-translation.html); ExPasy (http://www.expasy.org/tools/). In one embodiment, the RNA and/or cDNA coding sequences are designed for optimal expression in the subject species for which administration is ultimately intended, as discussed herein. Thus, in one embodiment, the coding sequences are designed for optimal expression in a feline. In another embodiment, the coding sequences are designed for optimal expression in a canine. In yet another embodiment, the coding sequences are designed for optimal expression in a primate.

The coding sequences may be designed for optimal expression using codon optimization. Codon-optimized coding regions can be designed by various different methods. This optimization may be performed using methods which are available on-line, published methods, or a company which provides codon optimizing services. One codon optimizing method is described, e.g., in International Patent Publication No. WO 2015/012924, which is incorporated by reference herein. Briefly, the nucleic acid sequence encoding the product is modified with synonymous codon sequences. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

The terms "percent (%) identity", "sequence identity", "percent sequence identity", or "percent identical" in the context of nucleic acid sequences refers to the bases in the two sequences which are the same when aligned for correspondence. The length of sequence identity comparison may be over the full-length of the genome, the full-length of a gene coding sequence, or a fragment of at least about 100 to 150 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 70 amino acids to about 100 amino acids, or a peptide fragment thereof or the corresponding nucleic acid sequence coding sequencers. A suitable amino acid fragment may be at least about 8 amino acids in length, and may be up to about 150 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

In one embodiment, the nucleic acid sequences encoding the EPO constructs described herein are engineered into any suitable genetic element, e.g., naked DNA, phage, transposon, cosmid, RNA molecule (e.g., mRNA), episome, etc., which transfers the EPO sequences carried thereon to a host cell, e.g., for generating nanoparticles carrying DNA or RNA, viral vectors in a packaging host cell and/or for delivery to a host cells in subject. In one embodiment, the genetic element is a plasmid. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

As used herein, an "expression cassette" refers to a nucleic acid molecule which comprises coding sequences for the EPO peptide, promoter, and may include other regulatory sequences therefor, which cassette may be engineered into a genetic element and/or packaged into the capsid of a viral vector (e.g., a viral particle). Typically, such an expression cassette for generating a viral vector contains the EPO construct sequences described herein flanked by packaging signals of the viral genome and other expression control sequences such as those described herein. Any of the expression control sequences can be optimized for a specific species using techniques known in the art including, e.g., codon optimization, as described herein.

The expression cassette typically contains a promoter sequence as part of the expression control sequences. In one embodiment, a CB7 promoter is used. CB7 is a chicken β-actin promoter with cytomegalovirus enhancer elements. Alternatively, other liver-specific promoters may be used [see, e.g., The Liver Specific Gene Promoter Database, Cold Spring Harbor, available online at rulai.schl.edu/LSPD, alpha 1 anti-trypsin (A1AT); human albumin Miyatake et al., J. Virol., 71:5124 32 (1997), humAlb; and hepatitis B virus core promoter, Sandig et al., Gene Ther., 3:1002 9 (1996)]. TTR minimal enhancer/promoter, alpha-antitrypsin promoter, LSP (845 nt)25 (requires intron-less scAAV). In one embodiment, the liver-specific promoter thyroxin binding globulin (TBG) is used. Other promoters, such as viral promoters, constitutive promoters, regulatable promoters

[see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, efficient RNA processing signals such as splicing and polyadenylation (polyA) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. The expression cassette or vector may contain none, one or more of any of the elements described herein. Examples of suitable polyA sequences include, e.g., SV40, bovine growth hormone (bGH), and TK polyA. Examples of suitable enhancers include, e.g., the CMV enhancer, the RSV enhancer, the alpha fetoprotein enhancer, the TTR minimal promoter/enhancer, LSP (TH-binding globulin promoter/alpha1-microglobulin/bikunin enhancer), amongst others.

In one embodiment, the viral vector includes a nucleic acid expression cassette comprising: a 5' AAV inverted terminal repeat sequence (ITR), a promoter with optional enhancer, an EPO sequence, a poly A sequence, and a 3' AAV ITR, wherein said expression cassette expresses a functional EPO in a host cell.

These control sequences are "operably linked" to the EPO construct sequences. As used herein, the term "operably linked" refers to both expression control sequences that are contiguous with the gene of interest and expression control sequences that act in trans or at a distance to control the gene of interest.

The expression cassette may be engineered onto a plasmid which is used for production of a viral vector. The minimal sequences required to package the expression cassette into an AAV viral particle are the AAV 5' and 3' ITRs, which may be of the same AAV origin as the capsid, or of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the propeptide-EPO active peptide coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

Exemplary plasmids are provided in the sequence listing. SEQ ID NO: 1 provides the sequence of a plasmid encoding a canine EPO construct, entitled pn1044.CB7.caEPO. In one embodiment, the expression cassette is engineered into the plasmid of SEQ ID NO: 1. SEQ ID NO: 2 provides the sequence of a plasmid encoding a feline EPO construct, entitled pn1044.CB7.feEPO. In one embodiment, the expression cassette is engineered into the plasmid of SEQ ID NO: 2. Plasmids, such as those, shown in SEQ ID NO: 1 and SEQ ID NO: 2 may be modified to include one or more additional components as described herein, or to remove or replace components as necessary. In one embodiment, the plasmid has the sequence of SEQ ID NO: 1 or a sequence sharing at least 80% identity therewith. In another embodiment, the plasmid has the sequence of SEQ ID NO: 2 or a sequence sharing at least 80% identity therewith.

The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

An adeno-associated virus (AAV) viral vector is an AAV DNase-resistant particle having an AAV protein capsid into which is packaged nucleic acid sequences for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAV serotypes may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, rh10, AAVrh64R1, AAVrh64R2, rh8, rh.10, variants of any of the known or mentioned AAVs or AAVs yet to be discovered. In one embodiment, the AAV is an AAV8 capsid, or a variant thereof. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10). Alternatively, a recombinant AAV based upon any of the recited AAVs, may be used as a source for the AAV capsid. These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV Caps or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV8 vp3. In another embodiment, a self-complementary AAV is used.

For packaging an expression cassette into virions, the ITRs are the only AAV components required in cis in the same construct as the gene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, N.Y. (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

Also provided are compositions which include the viral vector constructs described herein. The pharmaceutical compositions described herein are designed for delivery to subjects in need thereof by any suitable route or a combination of different routes. Direct delivery to the liver (optionally via intravenous, via the hepatic artery, or by transplant), oral, inhalation, intranasal, intratracheal, intraarterial, intraocular, intravenous, intramuscular, subcutaneous, intradermal, and other parental routes of administration. The viral vectors described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

The replication-defective viruses can be formulated with a physiologically acceptable carrier for use in gene transfer and gene therapy applications. In the case of AAV viral vectors, quantification of the genome copies ("GC") may be used as the measure of the dose contained in the formulation or suspension. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal).

Also, the replication-defective virus compositions can be formulated in dosage units to contain an amount of replication-defective virus that is in the range of about $1.0 \times 10^9$ GC to about $1.0 \times 10^{15}$ GC. In another embodiment, this amount of viral genome may be delivered in split doses. In one embodiment, the dosage is about $1.0 \times 10^{10}$ GC to about $1.0 \times 10^{12}$ GC for an average feline or small canine subject of about 5 kg. In one embodiment, the dosage is about $1.0 \times 10^{11}$ GC to about $1.0 \times 10^{13}$ GC for an average medium canine subject of about 20 kg. The average canine ranges from about 5 to about 50 kg in body weight. In one embodiment, the dosage is about $1.0 \times 10^{11}$ GC to $1.0 \times 10^{13}$ GC for a subject. In another embodiment, the dose about $3 \times 10^{12}$ GC. For example, the dose of AAV virus may be about $1 \times 10^{11}$ GC, about $5 \times 10^{11}$ GC, about $1 \times 10^{12}$ GC, about $5 \times 10^{12}$ GC, or about $1 \times 10^{13}$ GC. In one embodiment, the dosage is about $3 \times 10^{10}$ GC/kg. In another example, the constructs may be delivered in an amount of about 0.001 mg to about 10 mg per mL. In one embodiment, the constructs may be delivered in volumes from 1 µL to about 100 mL for a veterinary subject. See, e.g., Diehl et al, J. Applied Toxicology, 21:15-23 (2001) for a discussion of good practices for administration of substances to various veterinary animals. This document is incorporated herein by reference. As used herein, the term "dosage" can refer to the total dosage delivered to the subject in the course of treatment, or the amount delivered in a single (of multiple) administration.

The above-described recombinant vectors may be delivered to host cells according to published methods. The rAAV, preferably suspended in a physiologically compatible carrier, diluent, excipient and/or adjuvant, may be administered to a desired subject including without limitation, a cat, dog, or other non-human mammalian subject. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and/or variants and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The viral vectors and other constructs described herein may be used in preparing a medicament for delivering an EPO construct to a subject in need thereof and/or for treating chronic kidney disease in a subject. Thus, in another aspect a method of treating chronic kidney disease is provided. The method includes administering a composition as described herein to a subject in need thereof. In one embodiment, the composition includes a viral vector containing an EPO expression cassette, as described herein. In one embodiment, the subject is a mammal. In another embodiment, the subject is a feline or canine. In yet another aspect a method of treating anemia is provided. The method includes administering a composition as described herein to a subject in need thereof. In one embodiment, the composition includes a viral vector containing an EPO expression cassette, as described herein. In one embodiment, the subject is a mammal. In another embodiment, the subject is a feline or canine.

In another embodiment, a method for treating chronic kidney disease in a feline is provided. The method includes administering an AAV viral vector comprising a nucleic acid molecule comprising a sequence encoding feline EPO. In another embodiment, a method for treating chronic kidney disease in a canine is provided. The method includes administering an AAV viral vector comprising a nucleic acid molecule comprising a sequence encoding canine EPO.

A course of treatment may optionally involve repeat administration of the same viral vector (e.g., an AAV8 vector) or a different viral vector (e.g., an AAV8 and an AAVrh10). Still other combinations may be selected using the viral vectors described herein. Optionally, the composition described herein may be combined in a regimen involving other drugs or protein-based therapies, including e.g., recombinant EPO. Optionally, the composition described herein may be combined in a regimen involving lifestyle changes including dietary and exercise regimens.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

A "subject" is a mammal, e.g., a human, mouse, rat, guinea pig, dog, cat, horse, cow, pig, or non-human primate, such as a monkey, chimpanzee, baboon or gorilla. As used herein, the term "subject" is used interchangeably with "patient".

As used herein, "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

Example 1

Construction of EPO Vectors

The amino acid sequences of canine and feline erythropoietin were obtained from Genbank. The amino acid sequences were backtranslated and codon optimized, followed by addition of a kozac consensus sequence, stop codon, and cloning sites. The sequences were produced by GeneArt, and cloned into an expression vector containing a chicken-beta actin promoter with CMV enhancer (p1044). The expression construct is flanked by AAV2 ITRs. The canine and feline constructs were packaged in an AAV serotype 8 capsid by triple transfection and iodixanol gradient purification and titered by Taqman quantitative PCR.

Example 2

AAV-Mediated Expression of Feline Erythropoietin in Cats

Three cats were treated with a single intramuscular injection of $3\times10^{10}$ genome copies per kilogram body weight (GC/kg) AAV8 expressing feline erythropoietin (FIG. 1). Blood samples were collected at the time of injection and periodically thereafter for measurement of hematocrit. Therapeutic phlebotomy was initiated on day 42 after vector injection. To date, the results have shown seen sustained expression of EPO for greater than 100 days.

Example 3

AAV-Mediated Expression of Canine Erythropoietin in Dogs

Figure 2:
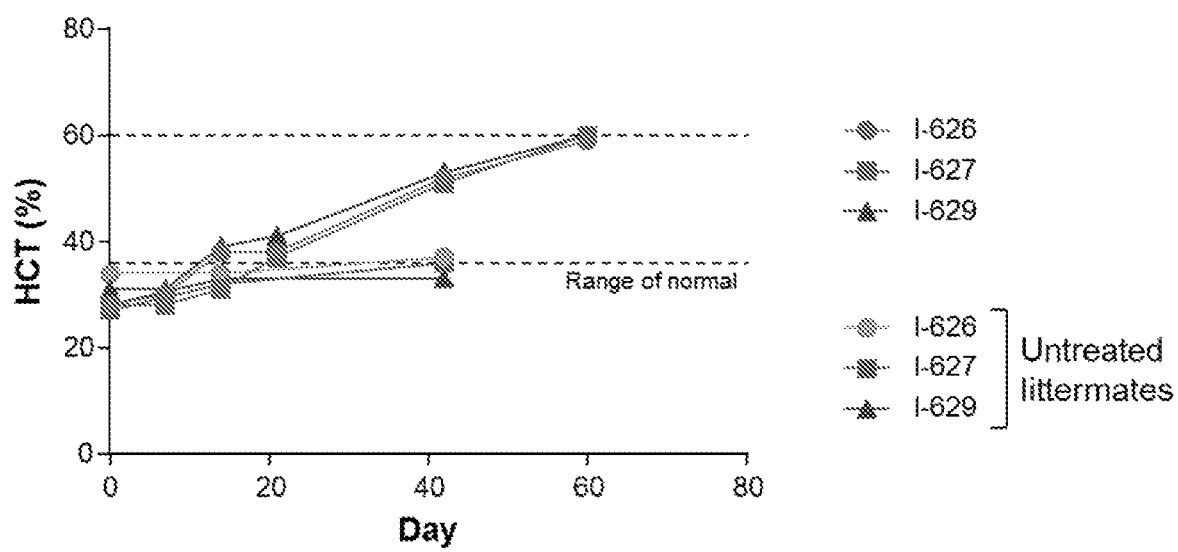
FIG. 2 is a graph showing hematocrits of dogs treated with AAV8 expressing canine erythropoietin. Dashed lines indicate the normal range.

Three dogs were treated with a single intramuscular injection of $3\times10^{10}$ GC/kg AAV8 expressing canine erythropoietin. Blood samples were collected at the time of injection and periodically thereafter for measurement of hematocrit (FIG. 2). Blood samples from untreated littermates were included as controls. Therapeutic phlebotomy was initiated on day 60 after vector injection.

Example 4

Dosage Study of AAV-Mediated Expression of Feline Erythropoietin in Cats

Figure 4:
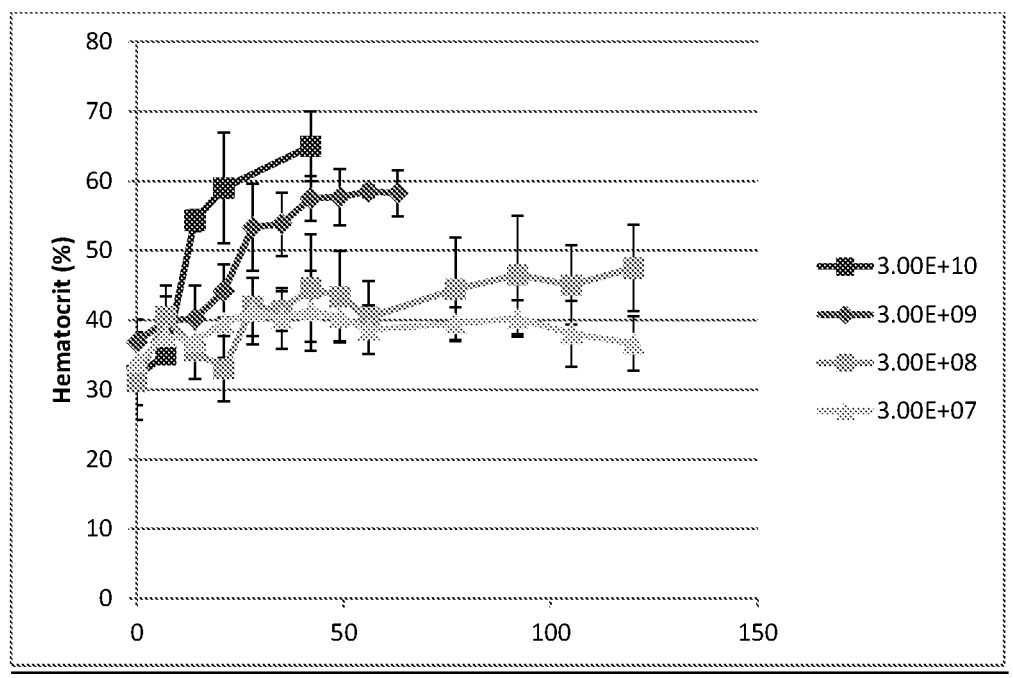
FIG. 4 is a graph showing hematocrits of cats treated with AAV8 expressing feline erythropoietin. Cats were treated with $3.0\times10^7$ GC, $3.0\times10^8$ GC, $3.0\times10^9$ GC, or $3.0\times10^{10}$ GC AAV8f.EPO.

Cats were treated with a single intramuscular injection of up to $3\times10^7$, $3\times10^8$, $3\times10^9$, or $3\times10^{10}$ genome copies per kilogram body weight (GC/kg) of AAV8 expressing feline erythropoietin. These three cohorts were of 4 cats per dosage. All cats were normal/wildtype and selected randomly. The purpose of this study was show long term safety and efficacy to highlight a possible clinical candidate for a client owned animal study. FIG. 4.

Example 5

AAV-Mediated Expression of Feline Erythropoietin in Cats

Cats are treated with a single intramuscular injection of up to $3\times10^9$ genome copies per kilogram body weight (GC/kg) AAV8 expressing feline erythropoietin in the left or right quadriceps in a total volume of up to 400 µL. Blood samples are collected at the time of injection and periodically thereafter for measurement of hematocrit. Vector may be readministered 28 days or more post the initial vector administration using the same criteria.

This study will include up to nine cats with anemia related to stage III chronic kidney disease. CKD related anemia will be defined as a hematocrit less than 29% on two occasions at least one month apart and without another apparent cause for the anemia. Enrolled subjects will receive a single intramuscular injection of an adenoassociated virus vector carrying a feline erythropoietin transgene (AAV8.fEpo). Subjects will be evaluated at the study site at the time of vector administration and at 2, 4, 6, and 8 weeks after administration. At each visit blood will be collected for evaluation of erythropoietin concentration, hematocrit, reticulocyte count, mean corpuscular volume, mean corpuscular hemoglobin, and mean corpuscular hemoglobin concentration. Patients will return to the study site or follow up with their primary veterinarian at 3 months, 6 months and 12 months after study drug administration for measurement of hematocrit. The study drug has previously been found to be safe in 4 normal cats at doses up to 3E8 genome copies/kg. The first three subjects enrolled in this trial will receive a dose of 1E8 genome copies/kg AAV8.fEpo. An initial evaluation of safety and vector activity will take place after the first three subjects have reached 8 weeks post vector administration. Depending on the results at the 8 week analysis in this initial cohort of 3 animals, dosing of the second cohort of three animals will proceed using the following scheme:
1. If any severe adverse events occur in the initial cohort or if any animal reaches a hematocrit 55%, the dose will be reduced threefold and three additional animals will be enrolled at this reduced dose. (total study enrollment of 6 subjects)
2. If there are no adverse events and all cats demonstrate an increase in hematocrit of at least 5% or reach the normal hematocrit range, 3 additional cats will be treated at the starting dose. (total study enrollment of 6 subjects)
3. If there are no adverse events and all cats do not achieve at least a 5% increase in hematocrit or reach the normal range, 3 additional cats will be treated at a 3fold higher dose of 3E8 genome copies/kg. There will again be an interim evaluation of safety and activity after all three animals in this cohort have reached 6 weeks post vector administration. If there are no adverse events and all cats demonstrate an increase in hematocrit of at least 5% or reach the normal hematocrit range, 3 additional cats will be treated at this dose. If there are no adverse events and all cats do not achieve at least a 5% increase in hematocrit or reach the normal range, 3 additional cats will be treated at a dose of 6E8 genome copies/kg. (total study enrollment of 9 subjects) This study will therefore enroll at least 6 and as many as 9 subjects depending on the results of interim analyses of safety and change in hematocrit. Primary endpoints include safety and evaluation of vector expression Secondary endpoints include quality of life for animals and long-term sustained expression of vector Inclusion criteria:

Cats with stage III renal failure (serum creatinine 2.95 mg/dL)

Hematocrit 29% on two occasions at least one month apart

Owner willing to return to study site for visits at 2 weeks, 4 weeks, 6 weeks, and 8 weeks after study drug administration, and to study site or primary veterinary clinic at 3 months, 6 months and 12 months after study drug administration.

Exclusion criteria:

Anticipated life expectancy less than 3 months

Kidney transplant

Past treatment with recombinant erythropoietin (epoetin, darbepoietin)

Any other condition that in the opinion of the principle investigator would preclude evaluation of the safety and activity of the study drug Preexisting neutralizing antibodies to AAV8

Eligible cats will be screened during first visit. This will include a full history and clinical exam, CBC/chemistry, and preexisting antibodies to AAV8, and full release on consent form.

All eligible cats that agree to terms of research protocol will receive a single intramuscular injection of AAV8.fEPO of up to 3E9 genome copies/kg at least one week after being accepted into study.

Following vector administration, cats will be evaluated every other week for a duration of 8 weeks. These clinical check ups will include CBC retic/chem, full clinical evaluation, and serum collection. After 8 weeks, these clinical evaluations will move to every 3 months, starting on day 90 after vector administration. The 3 month, 6 month, 9 month, and 1 year evaluations will be done.

Possible Complications

Any animal that displays polycythemia of 65% Hematocrit will be given a therapeutic phlebotomy of up to 10% blood volume per every 3 weeks.

All publications cited in this specification, as well as provisional patent application Nos. 62/212,144 and 62/336, 211 are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

What is claimed is:

1. A recombinant adeno-associated virus (rAAV) comprising an AAV capsid having packaged therein a vector genome, wherein said vector genome comprises a nucleotide sequence encoding a functional feline erythropoietin (EPO), inverted terminal repeat sequences, and expression control sequences that direct expression of the EPO in a host cell,
wherein the nucleotide sequence encoding the feline EPO comprises nucleotides 79 to 576 of the nucleotide sequence of SEQ ID NO: 8 and encodes at least amino acids 27 to 192 of the amino acid sequence of SEQ ID NO: 4.

2. The rAAV of claim 1, wherein the encoded feline EPO comprises the amino acids 27 to 192 of SEQ ID NO: 4 in combination with a heterologous leader sequence.

3. The rAAV of claim 1, wherein the EPO nucleotide sequence encodes amino acids 1 to 192 of SEQ ID NO: 4.

4. The rAAV of claim 3, wherein the nucleotide sequence encoding the feline EPO comprises SEQ ID NO: 8.

5. The rAAV of claim 1, wherein the expression control sequences comprise a promoter.

6. The rAAV of claim 5, wherein the promoter is selected from a CB7 promoter, a TBG promoter, a Nkcc2 promoter, a uromodulin promoter, a Ksp-cadherin promoter, and a THP gene promoter.

7. The rAAV of claim 1, wherein the expression control sequences comprise one or more of an intron, a Kozak sequence, a polyA, and post-transcriptional regulatory elements.

8. The rAAV of claim 1, wherein the AAV capsid is an AAV8, an AAVrh64R1, an AAV9, an AAVhu.37, an AAVrh10 capsid, or a variant thereof.

9. The rAAV of claim 1, wherein the capsid is an AAV8 capsid.

10. A pharmaceutical composition comprising a pharmaceutically acceptable carrier and the rAAV according to claim 1.

11. A recombinant adeno-associated virus (rAAV) comprising an AAV capsid having packaged therein a vector genome, wherein said vector genome comprises a nucleotide sequence encoding a functional canine EPO, inverted terminal repeat sequences, and expression control sequences that direct expression of the EPO in a host cell,
wherein the nucleotide sequence encoding the canine EPO comprises nucleotides 121 to 618 of the nucleotide sequence of SEQ ID NO: 7 and encodes at least amino acids 41 to 206 of the amino acid sequence of SEQ ID NO: 3.

12. The rAAV of claim 11, wherein the EPO nucleotide sequence encodes amino acids 1 to 206 of SEQ ID NO: 3.

13. The rAAV of claim 12, wherein the nucleotide sequence encoding the canine EPO comprises SEQ ID NO: 7.

14. The rAAV of claim 11, wherein the encoded canine EPO amino acid sequence comprises the amino acids 41 to 206 of SEQ ID NO: 3 in combination with a heterologous leader sequence.

15. The rAAV of claim 11, wherein the expression control sequences comprise a promoter.

16. The rAAV of claim 15, wherein the promoter is selected from a CB7 promoter, a TBG promoter, a Nkcc2 promoter, a uromodulin promoter, a Ksp-cadherin promoter, and a THP gene promoter.

17. The rAAV of claim 11, wherein the expression control sequences comprise one or more of an intron, a Kozak sequence, a polyA, and post-transcriptional regulatory elements.

18. The rAAV of claim 11, wherein the AAV capsid is an AAV8, an AAVrh64R1, an AAV9, an AAVhu.37, an AAVrh10 capsid, or a variant thereof.

19. The rAAV of claim 11, wherein the capsid is an AAV8 capsid.

20. A pharmaceutical composition comprising a pharmaceutically acceptable carrier and the rAAV according to claim 11.

* * * * *